(12) United States Patent
Zanellato et al.

(10) Patent No.: US 7,759,095 B2
(45) Date of Patent: Jul. 20, 2010

(54) PROCESS FOR THE PREPARATION AND ISOLATION OF PHOSPHATIDES

(75) Inventors: Anna Maria Zanellato, Bovolenta (IT); Mara Pittarello, Abano Terme (IT); Antonio Gambillara, Torreglia (IT); Susanna Vaccaro, Siracusa (IT)

(73) Assignee: Fidia Farmaceutici S.p.A., Abano Terme (IT)

( * ) Notice: Subject to any disclaimer, the term of this patent is extended or adjusted under 35 U.S.C. 154(b) by 361 days.

(21) Appl. No.: 11/922,680

(22) PCT Filed: May 26, 2006

(86) PCT No.: PCT/EP2006/005030

§ 371 (c)(1),
(2), (4) Date: Dec. 19, 2007

(87) PCT Pub. No.: WO2006/128639

PCT Pub. Date: Dec. 7, 2006

(65) Prior Publication Data

US 2008/0275006 A1    Nov. 6, 2008

(30) Foreign Application Priority Data

May 30, 2005    (IT) .......................... PD2005A0164

(51) Int. Cl.
*C12P 13/00*    (2006.01)
(52) U.S. Cl. ....................... 435/128; 426/531; 435/196; 514/114
(58) Field of Classification Search ....................... None
See application file for complete search history.

(56) References Cited

U.S. PATENT DOCUMENTS

| 3,869,482 A | 3/1975 | Wolfe |
| 2003/0012416 A1 | 7/2003 | Petrescu et al. |
| 2004/0235119 A1 | 11/2004 | Hoppe et al. |
| 2004/0235795 A1 | 11/2004 | Jager et al. |

FOREIGN PATENT DOCUMENTS

| EP | 0 285 421 A2 | 10/1988 |
| EP | 0 399 544 A1 | 11/1990 |
| EP | 0 711 559 A2 | 5/1996 |
| GB | 1 388 094 | 7/1973 |
| WO | WO 93/21190 | 10/1993 |
| WO | WO 00/77182 A1 | 12/2000 |
| WO | WO 03/088761 A2 | 10/2003 |
| WO | WO 2005/023271 A1 | 3/2005 |
| WO | WO 2005/068644 A1 | 7/2005 |

OTHER PUBLICATIONS

Bigon et al., "Pharmalogical Effects of Phosphatidylserine Liposomes: The Role of Lysophosphatidylserine," Br. J. Pharmac. 67:611-616 (1979).
Biton et al., "Pharmacological Effects of Phosphatidyserine Liposomes: Regulation of Glycolysis and Energy Level in Brain," Br. J. Pharmac. 66:167-174 (1979).
Toffano et al., "Central Pharmacological Effects of Phosphatidylserine Liposomes,"New Trends in Nutrition, Lipid Research, and Cardiovascular Disease, pp. 91-99 (1987).
Vasant V. Ranade, Ph.D., "Drug Delivery System, 1. Site-Specific Drug Delivery Using Liposomes as Carriers," J. Clin. Pharmacol. 29:685-694 (1989).

*Primary Examiner*—Herbert J. Lilling
(74) *Attorney, Agent, or Firm*—Porzio, Bromberg & Newman, P.C.

(57) ABSTRACT

Process for the preparation of phosphatidylserine of formula

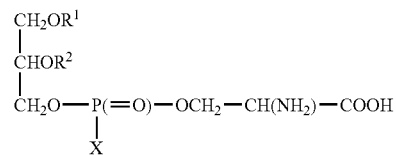

wherein $R^1$ and $R^2$ independently represent a saturated, mono-unsaturated or polyunsaturated acyl $C_{10}$-$C_{30}$, X=OH or OM where M=alkaline or alkaline earth metal, ammonium, alkylammonium (including the inner salt) including the transphosphatidylation reaction between phosphatidylcholine of the general formula

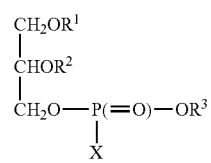

wherein $R^1$ and $R^2$ and X have the above specified meanings, $R^3$=$CH_2$—$CH_2$—$NH_2$ o $CH_2$—$CH_2$—$N^+(CH_3)_3$ and Serine in D, L or racemic form catalized by the phospholipase D enzyme (PLD),
  characterized in that said reaction is carried out in a hydroalcoholic medium containing an aliphatic alcohol and in the presence of bivalent metal oxide.

44 Claims, 4 Drawing Sheets

PLD

PROCESS FOR THE PREPARATION AND ISOLATION OF PHOSPHATIDES

SUBJECT OF THE INVENTION

The present invention relates to processes for the production and purification of phosphatidylserine (PS), to obtain the final product in high yield by means of bivalent metal oxides (BMO).

FIELD OF THE INVENTION

The functional decline of the Central Nervous System (CNS) that occurs during the physiological process of cerebral aging often causes deterioration of the cognitive functions in the elderly that may in turn cause behavioural disorders and alterations of the temporal and spatial memory.

This functional decline in CNS activity is linked with both the onset of biochemical and structural alterations in the lipid composition of the neuronal membranes and decreased activity of the cerebral enzymes that may reduce neuronal synapses.

Phosphatidylserine (PS) is the main acidic phospholipid in the brain. Scientific research has therefore been focused for some time on finding a pharmacological treatment for age-related cognitive disorders, based on phospholipids that can prevent (and/or partially reconstruct) the structural and functional deficit of aging neuronal membranes.

Preclinical and clinical studies in humans have demonstrated that administering PS orally can, especially in the elderly, determine a significant increase in learning capacity and temporal and spatial memory, even in the case of particularly disabling pathologies such as Alzheimer's disease (Cenacchi T. et al.; Aging Clin Exp Res; 1993; 5:123-133; Nunzi M G et al.; Adv Exp Med Biol; 1992; 318:393-8).

Moreover, it has been demonstrated that phosphatidylserine is able to combat the increase in the hormone cortisol in subjects undergoing physical stress (Monteleone P. et al.; Neuroendocrinology; 1990; 52(3):243-8), thereby lessening the catabolism of glucose, with greater functional recovery after intense physical effort.

The present invention relates to a process for the synthesis and purification of PS and to the use of PS as the active principle in drugs (and/or food supplements) for the prevention of the aforesaid age-related pathologies, and in the preparation of food supplements indicated for all cases of intense physical stress and, moreover, in the production of liposomes for use in the field of cosmetics and/or as a controlled release system for the drugs they contain.

The processes for producing and purifying PS already known from the scientific literature and patents describe the enzymatic conversion of phosphatidylcholine (PC) into PS by a transphosphatidylation reaction catalysed by the enzyme phospholipase D (PLD), with subsequent purification brought about mainly by extracting the PS with organic solvents.

In recent years, various processes have been perfected for synthesising PS by enzymatic conversion in two-phase systems of water/organic solvent or in an aqueous medium.

EP 0776976 describes a process for the enzymatic preparation of PS in a system consisting of water/toluene wherein the organic phase contains the starting phospholipid from which PS is formed, the aqueous phase contains the hydroxy acceptor and the synthesis reaction occurs in the water/solvent interface in the presence of crude phospholipase D from fermentation broths of strains of micro-organisms producing PLD.

For the first time, in 1990, researchers attempted to sidestep the two-phase system because it required large quantities of solvent that was then difficult to eliminate, with consequently high costs for the production and purification of PS (Comfurius P. et al., Journal of Lipid Research 1990, 31:1719-1721).

The organic solvent was therefore substituted by a detergent/surfactant capable of dispersing the starting phospholipid in micellar form in order to bring about the enzymatic reaction of synthesis exclusively in an aqueous medium.

Indeed, EP 1048738 relates to a process for the enzymatic synthesis of PS in an aqueous medium absolutely free from any contamination by organic solvents, in the presence of given concentrations of specific detergents and calcium salts.

DE 19917249 describes a method for the enzymatic production of PS in an aqueous medium without using surfactants, exclusively with the addition of calcium chloride salt ($CaCl_2$), however, the percentage of enzymatic conversion and the degree of purity of the PS obtained are not specified.

EP 1310563 discloses a process for the preparation of PS in an aqueous phase without using detergents and/or calcium salts, based on the homogenisation of the starting mixture consisting of phospholipid, hydroxy acceptor and PLD in water, to give a final homogenate with a structure similar to that of a bi-lamellar phospholipid membrane wherein the transphosphatidylation reaction can subsequently occur.

EP 1427839 describes the enzymatic synthesis of phospholipids, including PS, in water, without detergents but in the presence of metal ions that are released from the corresponding salts when they are prepared/dissolved in water. Said process occurs in two distinct phases in which, starting from mixtures of phospholipids, a first enzymatic hydrolysis reaction is catalysed by PLD to produce phosphatidic acid, followed by a second transphosphatidylation reaction in which PS is formed in the presence of an excess of serine.

Lastly, EP 12312134 claims a process for the enzymatic synthesis of PS using, in water, a fraction of the enzyme PLD produced and purified from the *Streptoverticillium hachijoense* strain for a more abundant yield in the final production of PS.

Concerning the purification of PS (obtained either by transphosphatidylation in an aqueous medium/organic solvent or in an aqueous medium), EP 1213294 claims a process of purification based on the use of a mixture consisting of water/polar organic solvent (such as isopropanol) to extract the abovesaid phospholipid from the solution that contains it, which is in turn represented by a hydrocarbon solvent (such as toluene), while EP 0922707 relates to a process for the extraction/purification of PS from a mixture of phospholipids using a diphasic system of organic solvents such as heptane and methanol.

The present invention relates to processes for the production and purification of phosphatidylserine (PS) that afford the final product in a very high yield thanks to an efficient conversion of PC into PS by the specific action of Bivalent Metal Oxides (BMO).

Moreover, the transphosphatidylation process catalysed by the enzyme PLD, enables a high percentage of PC to be converted into PS regardless of the medium in which the enzymatic reaction occurs.

Therefore, the present invention relates to a process for the production of PS catalysed by PLD and BMO, which process is characterized in that it is carried out in a hydroalcoholic medium consisting of water/aliphatic alcohols, or in an aprotic medium consisting of water/polar aprotic solvents, or in a two-phase system consisting of water/organic solvents.

DETAILED DESCRIPTION OF THE INVENTION

The present invention relates to a process for the preparation of PS (formula I), in which a transphosphatidylation is carried out by the enzyme PLD, in the presence of BMO, thereby attaining the transfer of a phosphatidyl moiety from phosphatidylcholine (PC) (formula II) to serine (which in this case represents the hydroxy acceptor); this enzymatic reaction provides the conversion of PC into PS in a very high degree regardless of the medium in which the enzymatic reaction occurs. Said reaction can therefore take place:

- in a hydroalcoholic medium consisting of water/aliphatic alcohols that do not form a two-phase system, or
- in an aprotic medium consisting of water/polar aprotic solvents that do not form a two-phase system, or
- in a two-phase system consisting of water/organic solvents.

Formula I wherein $R^1$ and $R^2$ independently represent a saturated, mono-unsaturated and/or poly-unsaturated acyl $C_{10}$-$C_{30}$, X=OH or OM where M=alkaline or alkaline earth metal, ammonium, alkylammonium (including the inner salt).

Formula II wherein $R^1$ and $R^2$ and X signify as defined above and $R^3 = CH_2-CH_2-NH_2$ or $CH_2-CH_2-N^+(CH_3)_3$.

It has surprisingly been found that BMO drastically modifies the reaction substrate represented by the starting phosphatidylcholine, determining a change such that the action of enzyme PLD significantly increases in terms of final yield in PS, thus enabling a highly advantageous production of PS on an industrial scale. This substantial change occurs in the structure of the substrate itself, regardless of the medium in which the enzymatic reaction takes place. Indeed, BMO favours the fissuration of the PC vesicles and, thereby, penetration of the enzyme therein, determining an increase in the percentage of conversion of PC into PS since, by penetrating inside the vesicles, the PLD enzyme can also act on the lipid layer inside the vesicle, which could not formerly be penetrated by hydrophilic solutions such as those that contain the enzyme itself.

According to the invention, various bivalent metal oxides were tested, such as Calcium oxide (CaO), Magnesium oxide (MgO) and Zinc oxide (ZnO), both in hydroalcoholic and in aprotic medium, as well as in two-phase systems in which they gave excellent results, as shown in the following Examples, compared to the results obtained by means of the same processes but in the presence of Calcium chloride ($CaCl_2$).

Indeed, it is known that Calcium salts, and in particular $CaCl_2$ as sources of Calcium ions added to the medium in which the transphosphatidylation reaction occurs (Comfurius P. et al., Journal of Lipid Research 1990, 31:1719-1721; Comfurius P. et al., Biochim Biophys Acta, 1977, 488:36-42), promote the catalytic activity of the PLD enzyme and thereby increase the phosphatidylcholine conversion into PS (Okawa Y. et al.; J. Biochem.; 1975; 78:363-372).

In order to differentiate and clarify that BMO are completely different from metal salts and to demonstrate their efficacy in the new production systems that are the subject of the present invention, the Applicant has performed experiments comparing the different yields from the conversion of PC into PS in the presence of Calcium salts and in the presence of BMO.

As can be seen from the results obtained, the yield from the conversion of phosphatidylcholine into PS consistently proved to be not only quite unlike, but also decidedly and significantly higher than that obtained with $CaCl_2$.

Besides the oxides described above, various different BMO can be used in the new process for the production of PS, such as Manganese oxide, bivalent Iron oxide, Cobalt oxide, Copper oxide and all the remaining bivalent metal oxides in the Table of Elements.

Example of solvents in which the process of the present invention can be carried out are aliphatic alcohols, such as methyl, ethyl, n-propyl, isopropanols; aprotic polar solvents, such as dimethylsulfoxide (DMSO), dimethylformamide, acetonitrile, N-methyl-pyrrolidone; and organic solvents, such as n-hexane, toluene, n-butanol, benzene.

The preferred alcohol is isopropanol, the preferred aprotic solvent is DMSO and the preferred organic solvent is hexane.

Example 1 describes the conversion of PC into PS starting from starting a hydroalcoholic medium containing given percentages of isopropanol added to an starting solution consisting of acetate buffer in which CaO (or MgO or ZnO) has been dissolved, compared to the PS production process performed in the same hydroalcoholic medium but in the presence of $CaCl_2$ salt.

The percentage of alcohol (isopropanol in particular) that can be used in the present process (expressed as % by volume on the volume of the starting buffer) may vary from 0.1 to 50%, preferably from 1.25 to 20%, and most preferably 10%, in a hydroalcoholic medium containing a concentration of BMO (in particular, CaO) varying between 0.1 and 1M, preferably between 0.3 and 0.6M and most preferably equal to 0.54M.

The maximum yield from the conversion of PC into PS is 90%, which is far removed from the yield obtained by the same production process but in the presence of $CaCl_2$.

Example 2, on the other hand, demonstrates that it is possible to obtain yields even higher than 80% from the conversion of PC/PS, by adding given quantities of DMSO (expressed as % by volume on the volume of buffer used) to the starting buffer solution containing given molar concentrations of CaO (or MgO or ZnO), and that the aforesaid yields of PS are very different from those obtained by the same production process but in the presence of $CaCl_2$.

The percentage of aprotic solvent (and DMSO in particular) to be used may vary from 0.1 al 50%, preferably from 1.25 to 10%, and most preferably be 1.25%, in an aprotic medium containing a concentration of BMO (CaO in particular) varying between 0.1 and 1M, preferably between 0.3 and 0.6 M, and even more preferably, it may be equal to 0.33M.

The enzymatic reaction of transphosphatidylation gives a very high yield of PC/PS conversion, even in a two-phase system consisting of water/organic solvent.

Example 3 describes the production of PS in a two-phase system consisting of water/hexane, again in the presence of CaO, MgO and ZnO. The quantity of solvent used in the new processes that are the subject of the present invention is very low (as demonstrated hereafter), so low that production costs are limited and it is not difficult to eliminate the solvent from the final product.

The concentration of solvent to be used in said process may vary from 0.1 to 40% v/v (expressed as % by volume on the volume of starting buffer), preferably from 1 to 5% v/v, and most preferably 1.25% v/v and 2.5% v/v, in the presence of BMO (and CaO in particular) at a concentration varying between 0.1 and 1M, preferably between 0.3 and 0.6M and most preferably equal to 0.54M.

In this case too the maximum yield from the conversion of PC into PS was over 80%, quite different from that obtained by the same process but in the presence of $CaCl_2$.

The transphosphatidylation reaction can be conducted at different temperatures, ranging between 20 and 70° C., preferably at 45 or 55° C.

The starting phosphatide substrate is represented by phosphatidylcholine of animal and/or vegetal origin, natural or synthetic, present in purified form or as the raw material, at starting concentrations ranging between 10 and 500 mg/ml, preferably between 200 and 300 mg/ml.

The starting aqueous medium to be mixed/associated with the alcohol, the aprotic solvent or the organic solvent to obtain a hydroalcoholic, aprotic or two-phase final medium, is represented by water or an unbuffered saline solution or a buffer solution formed, for example, by sodium acetate trihydrate and acetic acid at concentrations of between 0.02 and 0.2M.

The hydroxyl acceptor is represented by serine, that may be present in D, L or racemic form. The optimal concentration of serine, preferably in L form, may vary between 1 g/g (gg) of starting phosphatide, up to 5 gg, preferably between 2 and 3 gg/gg of phosphatide.

The optimal pH of the buffer solution may vary between 4 and 9 because it depends on the origin of the PLD used, but preferably between 5 and 6, and most preferably equal to 5.6 if a PLD of fermentative origin derived from the microorganism *Streptoverticillium hachijoense* is used.

Said enzyme can be used in purified or partially purified form, or in a non-purified form after simple filtration of the micro-organism from its culture broth.

Example 4 (and FIG. 1) describes a new system for the partial purification of PLD to obtain an enzyme that is substantially not contaminated by proteins of a different nature that might interfere with the catalytic activity of PLD, a process which does not involve too many steps, since lengthy processes lead to excessive industrial costs and a consequent lack of feasibility on an industrial scale.

The partially purified enzyme described in Example 4 was tested in the production process described in Example 3, in comparison to an enzyme present in non-purified form (after simple elimination of the producer micro-organism) and to highly purified enzymatic preparations (obtained using ion exchange chromatographic resins and mono/polyclonal antibodies directed towards the PLD enzyme, but which may also be purified using all the purification methods known to a skilled in the art): the percentage of PC/PS conversion was equal for all the enzymatic preparations tested (purified, partially purified and non-purified).

The optimal quantity of PLD to ensure over 80% conversion of PC into PS ranges between 1 and 100 units/g of starting phosphatide, because it depends upon the origin of the PLD used. For example, when PLD from *Streptoverticillium hachijoense* is used, the optimal concentration varies between 1 and 10 units/g of phosphatide.

Another object of the present invention is a process for the separation and purification of PS from serine, PC and PLD (which represent impurities) remaining in the medium in which the transphosphatidylation reaction has taken place.

In order to separate and purify PS, the following methods have been developed.

1. at the end of the enzymatic transphosphatidylation reaction, the PS is separated by adding a solution of sodium chloride, at a concentration of between 2 and 6% (preferably 5%), to the reaction medium in which the newly-produced phospholipid is present: two phases will thus be obtained because the PS remains insoluble in this solution while the residue components (that are most soluble) mostly remain in the subnatant. The PS, which has been deposited in the upper part of the reaction medium, is then isolated by separating and eliminating the subnatant.

Alternatively, it is possible to start a new process of separation and purification of PS, object of the present invention, by filtering the PS container in the reaction medium to eliminate immediately all its residue components. A solution of NaCl is then added. Two phases form and the supernatant is eliminated because the PS is found in the subnatant. NaCl washings can be repeated twice or more times, adjusting the salt concentration if necessary. These washing procedures enable the complete elimination of the alcohols, aprotic and organic solvents used in the processes to produce PS described above, as demonstrated in Example 5. Subsequently, after treatment of the ions present in the reaction medium with a chelating agent, the product is precipitated/washed with a ethanol solution (at a percentage of between 50 and 100%, preferably 95%), or with a mixture of ketone solvents (such as acetone) in water (at a percentage of between 50 and 95%); washing with ethanol can be repeated several times (adjusting the percentage of ethanol present, if necessary). Lastly, a final wash is performed with ethanol at between 90 and 100%, after which the finished product may or may not be dried;

2. the separation and purification of PS is carried out by ultrafiltration, at the end of the transphosphatidylation enzymatic reaction, using a porous membrane of pore size such as to allow the passage of small molecules while trapping large ones. For this reason, it is preferable to use filters with pores small enough to trap molecules with a molecular weight of 100,000/300,000 Daltons or over.

Said procedures for the isolation and purification of PS enable elimination of the residues of the substances that are left after enzymatic reaction and were initially contained in the transphosphatidylation medium such as serine, PC, mineral salts, choline that is released from PC, PA, salts/oxides, and, above all, enable the complete purification of the PS from the PLD enzyme, no trace of which, as demonstrated in Example 5, remains. The final PS thus obtained has a very high degree of purity.

Some antioxidants such as ascorbic acid and/or vitamin E can be included in the process of preparation and purification of PS.

The invention is disclosed in more detail in the following examples.

EXAMPLE 1

Preparation of PS from Vegetal PC in a Hydroalcoholic Medium (by the Presence of Isopropanol) with CaO, MgO and ZnO 0.54M or with $CaCl_2$ 0.54M Two different hydroalcoholic solutions were prepared, formed by two concentrations of isopropanol (equal to 1.25 and 10% of the volume of the starting buffer) in acetate buffer containing CaO (or MgO or ZnO) 0.54M, compared to the preparation of PS by the same procedure but in the presence of $CaCl_2$ salt, 0.54M.

The tested oxides and Calcium chloride are dissolved in 40 ml of acetate buffer 0.2 M (pH 5.6) to which is then added 0.5 ml of isopropanol in order to reach 1.25% v/v (only for CaO), or 4 ml of isopropanol in order to reach 10% v/v (the alcohols can also be added to the buffer containing BMO after solubilisation of the Serine).

The resulting solutions are stirred in a jacketed reactor with condenser for about 10 minutes, then 20 g of L-serine is added at a temperature of 55° C., stirring until complete dissolution. Subsequently, 10 g of soy phosphatidylcholine is added and stirred for 10 minutes. 5.5 U of PLD enzyme per gg of PC is then added and the mixture is stirred for 24-48 hours at 55° C.

Finally, a sample of each product is taken and the successful transformation of PC into PS is tested by Thin Layer Chromatography (TLC).

Yield from the conversion of PC into PS:

distribution of the products present at the end of the reaction, expressed as % of PA (phosphatidic acid released by the PC as a result of the action of PLD) and PS obtained following the transphosphatidylation process. PA and PC are to be considered residues from the reaction.

Yield from the conversion of PC into PS obtained with isopropanol, 1.25% v/v, in the presence of CaO:
PA 8.0%
PS 85.5%
PC 6.5%

Yield from the conversion of PC into PS obtained with isopropanol, 10% v/v, in the presence of CaO:
PE-OH 4.0%
PA 3.5%
PS 89.5%
PC 3.0%

Yield from the conversion of PC into PS obtained with isopropanol, 10% v/v, in the presence of $CaCl_2$:
PE-OH 15.8%
PA 10.7%
PS 70.1%
PC 3.4%

Yield from the conversion of PC into PS obtained with isopropanol, 10% v/v, in the presence of MgO:
PE-OH 9.0%
PA 4.5%
PS 84.0%
PC 2.5%

Yield from the conversion of PC into PS obtained with isopropanol, 10% v/v, in the presence of ZnO:
PE-OH 10.0%
PA 8.0%
PS 80.0%
PC 2.0%

(the product defined as PE-OH forms during the transphosphatidylation reaction because the reaction occurs in the presence of alcohol).

EXAMPLE 2

Preparation of PS from Vegetal PC in an Aprotic Medium (by the Presence of DMSO) with CaO, MgO and ZnO 0.33M or with $CaCl_2$ 0.33M DMSO was used at different concentrations varying between a percentage of 1.25 and 10% in terms of the volume of starting buffer, in all cases in the presence of CaO (or MgO or ZnO) 0.33M in comparison with the preparation of PS by the same process but in the presence of $CaCl_2$ salt.

The Calcium oxides tested and Calcium chloride are dissolved in 40 ml of acetate butter 0.2 M, at pH 5.6. The solutions thus obtained are stirred in a jacketed reactor with condenser. After about 10 minutes' stirring, 20 g of L-serine is added at a temperature of 45° C. and then stirring is continued until complete solubilisation is achieved.

Subsequently, 10 g of soy PC and 0.5 ml of DMSO (corresponding to 1.25% v/v) or 4 ml of DMSO (corresponding to 10% v/v) are added and the mixture is stirred (the DMSO may be added during the starting phase of the process, after solubilisation of the BMO, as in the previous Example). Ten minutes later, 5.5 U of PLD enzyme per gg of PC is added, and the mixture is stirred for 24-48 hours at 45° C.

Subsequently, samples of the respective products obtained are taken at the end of the reaction and tested for the successful transformation of PC into PS.

Yield from the conversion of PC into PS:

Yield from the conversion of PC into PS obtained with DMSO 1.25% v/v in the presence of CaO:
PA 7.1%
PS 86.3%
PC 6.6%

Yield from the conversion of PC into PS obtained with DMSO 1.25% v/v in the presence of $CaCl_2$:
PA 8.1%
PS 66.7%
PC 25.2%

Yield from the conversion of PC into PS obtained with DMSO 10% v/v in the presence of $CaCl_2$:
PA 6%
PS 69%
PC 25%

Yield from the conversion of PC into PS obtained with DMSO 10% v/v in the presence of CaO:
PA 7.5%
PS 72.5%
PC 20%

Yield from the conversion of PC into PS obtained with DMSO 10% v/v in the presence of MgO:
PA 9.0%
PS 71.0%
PC 20%

Yield from the conversion of PC into PS obtained with DMSO 10% v/v in the presence of ZnO:
PA 8.5%
PS 71.5%
PC 20%

EXAMPLE 3a

Preparation of PS from Vegetal PC in a Two-Phase System (by the Presence of the Organic Solvent, Hexane) with CaO, MgO and ZnO 0.54M or with $CaCl_2$ 0.54M A two-phase system consisting of acetate buffer containing CaO (or MgO or ZnO) 0.54M was prepared, and then a quantity of hexane equal to 1.25% of the starting volume of the buffer was added, compared to the preparation of PS by the same production process but in the presence of $CaCl_2$, 0.54M.

The oxides tested and Calcium chloride are then dissolved in 40 ml of acetate buffer 0.2 M (pH 5.6) to which a quantity of hexane equal to 0.5 ml is then added in order to reach 1.25% v/v (the organic solvent of choice can be added to the buffer containing the BMO before or after solubilisation of the serine).

The solutions thus obtained are stirred in a jacketed reactor with condenser.

The procedure then continues as described in Example 1.

Finally, a sample of each product obtained is taken and tested for the successful transformation of PC into PS.

Yield from the conversion of PC into PS:

Yield from the conversion of PC into PS obtained with hexane 1.25% v/v in the presence of CaO:
PA 7.5%
PS 87.0%
PC 5.5%

Yield from the conversion of PC into PS obtained with hexane 1.25% v/v in the presence of $CaCl_2$:
PA 8.1%
PS 68.4%
PC 23.5%

Yield from the conversion of PC into PS obtained with hexane 1.25% v/v in the presence of MgO:
PA 8.5%
PS 82.5%
PC 9.0%

Yield from the conversion of PC into PS obtained with hexane 1.25% v/v in the presence of ZnO:
PA 11.0%
PS 80.0%
PC 9.0%

EXAMPLE 3b

Preparation of PS from Vegetal PC in a Two-phase System (by the Presence of the Organic Solvent, Hexane) with CaO 0.54M or with $CaCl_2$ 0.54M A two-phase system consisting of acetate buffer containing CaO 0.54M was prepared and then a quantity of hexane equal to 2.5% of the starting volume of the buffer was added, compared to the preparation of PS by the same production process but in the presence of $CaCl_2$, 0.54M. From this point on, the procedure is the same as in Example 3a.

Yield from the conversion of PC into PS:

Yield from the conversion of PC into PS obtained with hexane 2.5% v/v in the presence of CaO:
PA 7.5%
PS 86.0%
PC 6.5%

Yield from the conversion of PC into PS obtained with hexane 2.5% v/v in the presence of $CaCl_2$:
PA 10.0%
PS 65.0%
PC 25.0%

EXAMPLE 4

Partial Purification of the PLD Enzyme

The PLD enzyme used in the new production process can be partially purified by the following steps:

elimination of the producing agent by tangential-flow microfiltration through filters (preferably with polyethersulphone membranes: PES) with a pore size of 0.2 µm;

tangential-flow ultrafiltration through filters (preferably in PES) with a molecular cut-off of 10,000 D;

tangential-flow ultrafiltration through filters with membranes (preferably in PES) with a molecular cut-off of 300,000 D;

final tangential-flow ultrafiltration through membranes (preferably in PES) with a molecular cut-off of 10,000 D to re-concentrate the enzyme and dialyse it against TRIS-HCL buffer, 50 mM pH=8.

Figure 1:
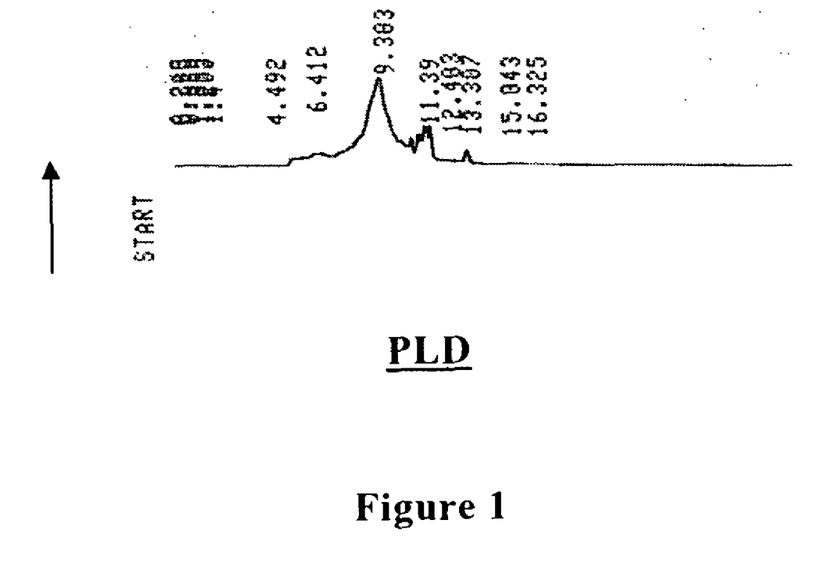
FIG. 1 is a graph of the chromatographic analysis of phospholipase D enzyme (PLD) after partial purification.
Figure 2:
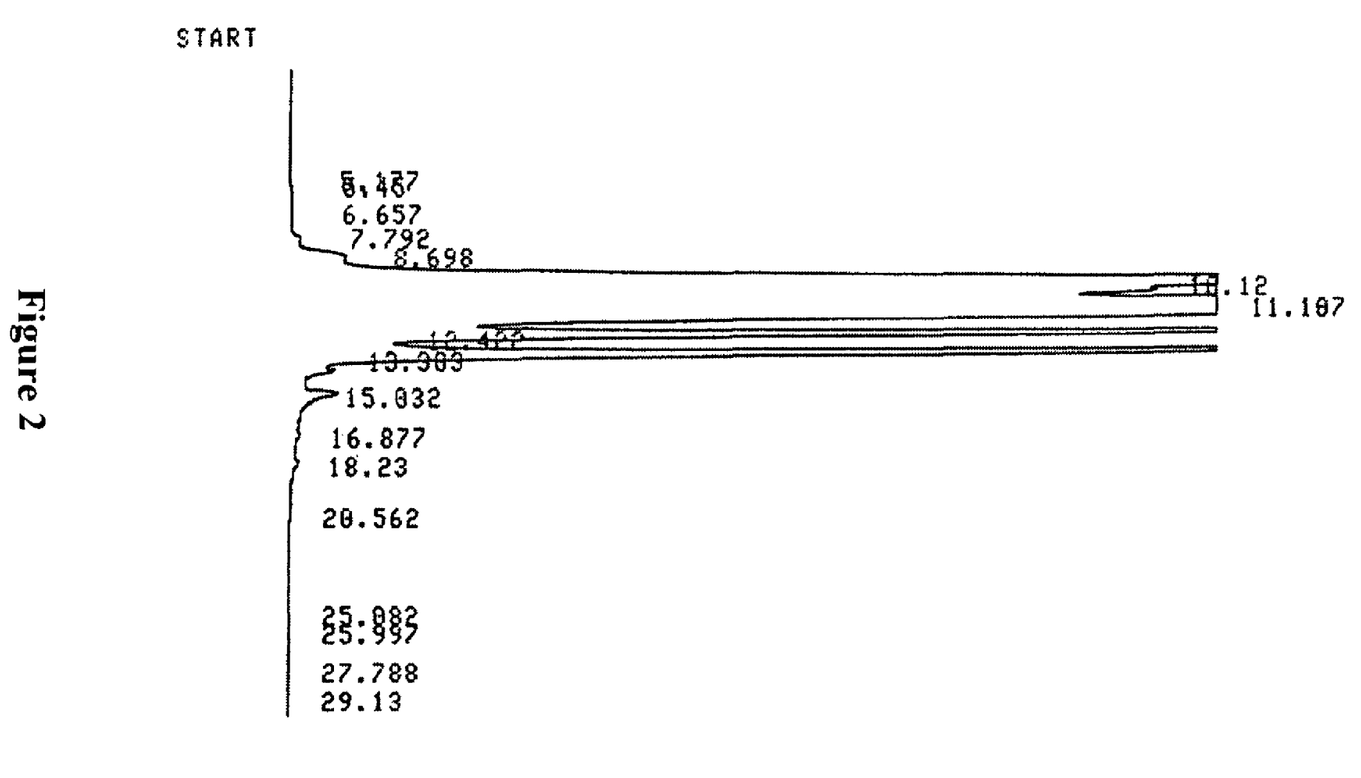
FIG. 2 is a graph of chromatographic analysis of fermentation of broth purified solely from the agent producing the PLD enzyme.

FIG. 1 shows the findings from chromatographic analysis of enzyme PLD partially purified as described above, compared with analysis of a fermentation broth purified solely from the agent producing the enzyme itself (FIG. 2).

EXAMPLE 5a

Separation and Purification of PS According to Method 1

The reaction medium in which the PS has been prepared is supplemented with 1.5 volumes (in terms of the starting reaction volume) of a 5% solution of NaCl, and the mixture is stirred at a temperature of 30° C. for at least 30 minutes. The PS, which has been deposited in the upper part of the reaction medium, is then isolated by separating and eliminating the subnatant. The supernatant (PS) is supplemented with 4 volumes of a 3% solution of NaCl and stirred at 30±10° C. for at least 30 minutes. Following that, the supernatant is separated and eliminated (this step has been repeated 2 times), while to the subnatant (represented by PS) is added 2 volumes of a solution of EDTA (ethylene diaminotetraacetic acid) (at a concentration of 40 gg/liter) prepared in an acetate buffer, 0.1 M pH 7.5.

After further mixing (at 25±10° C. for at least 1 hour) by stirring the mixture thus obtained, the pH is adjusted to 7/7.5 and 2 volumes (in terms of the volume of EDTA) of 95% ethanol are added, stirring the mixture at 25±10° C. for at least 1 hour.

After a period of sedimentation of the PS, it is collected and the supernatant (the phase consisting of ethanol in water) is eliminated because PS will not dissolve in a hydroalcoholic phase. Washing with ethanol/water (with a percentage of ethanol of 70-95%) has been repeated after which a final washing with 100% ethanol is performed, and as a final step the PS can be dried.

Final product: distribution of the lipid fractions isolated according to method 1, with PS prepared as described in Example 3 with CaO 0.54M.

PA 5.8%
PS 94.2%

EXAMPLE 5b

Separation and Purification of PS According to Method 1

The reaction medium in which the PS has been prepared is supplemented with 1.5 volumes (in terms of the starting reaction volume) of a 5% solution of NaCl, and the mixture is stirred at a temperature of 20° C. for at least 30 minutes. The PS, which has been deposited in the upper part of the reaction medium, is then isolated by separating and eliminating the subnatant. The supernatant (PS) is supplemented with 3 volumes of a 3% solution of NaCl and stirred at 20±10° C. for at least 30 minutes. Following that, the supernatant is separated and eliminated (this step has been repeated 3 times), while to the subnatant (represented by PS) is added 3 volumes of a solution of EDTA (at a concentration of 30 gg/liter) prepared in an acetate buffer, 0.1 M pH 7.0.

After further mixing (at 20±10° C. for at least 1 hour) by stirring the mixture thus obtained, the pH is adjusted to 7/7.5 and 2 volumes (in terms of the volume of EDTA) of 100% ethanol are added, stirring the mixture at 20±10° C. for at least 1 hour.

After a period of sedimentation of the PS, it is collected and the supernatant (the phase consisting of ethanol in water) is eliminated. Washing with ethanol/water (with a percentage of ethanol of 70%) has been repeated after which a final washing with 100% ethanol is performed, and as a final step the PS can be dried.

Final product: distribution of the lipid fractions isolated according to method 1, with PS prepared as described in Example 3 with CaO 0.54M.
PA 6.8%
PS 93.2%

EXAMPLE 5c

Separation and Purification of PS According to Method 1

Before adding the NaCl solution, the PS is filtered to eliminate immediately all the residue components of the reaction medium. Then NaCl is added and the isolation and purification process is continued as described in Example 5a.

Final product: distribution of the lipid fractions isolated according to method 1, with PS prepared as described in Example 3 with CaO 0.54M.
PA 5.0%
PS 95.0%

After the transphosphatidylation reaction, TLC analysis of the product obtained (Vitello F. et al.; J Chromatog; 1978; 166(2):637-40) shows a 2% concentration of residue serine.

The quantity of PLD in this phase was determined by state of the art methods (Aurich I. et al.; Anal Biochem; 1999; 268:337-342) and proved to be 2 U/g.

The serine concentration was measured again at the end of the process for the purification of PS described previously and proved to be lower than/equal to 0.2%.

The residue activity of the PLD enzyme was also determined again and proved to be below the limit for determination by this method.

To demonstrate the total absence of even the smallest trace of organic solvent used in the process of preparing PS (described in Example 3) and thus confirm the novelty and inventive step of the present invention, the Applicant analysed the partially purified PS described in Example 5, in the phase immediately preceding the addition of the alcoholic solution.

This analysis was performed by the known technique of "Gas chromatography with static head-space injection" as described in the European Pharmacopoeia 5.0, section 2.4.24: Identification and control of residual solvents.

Figure 3:
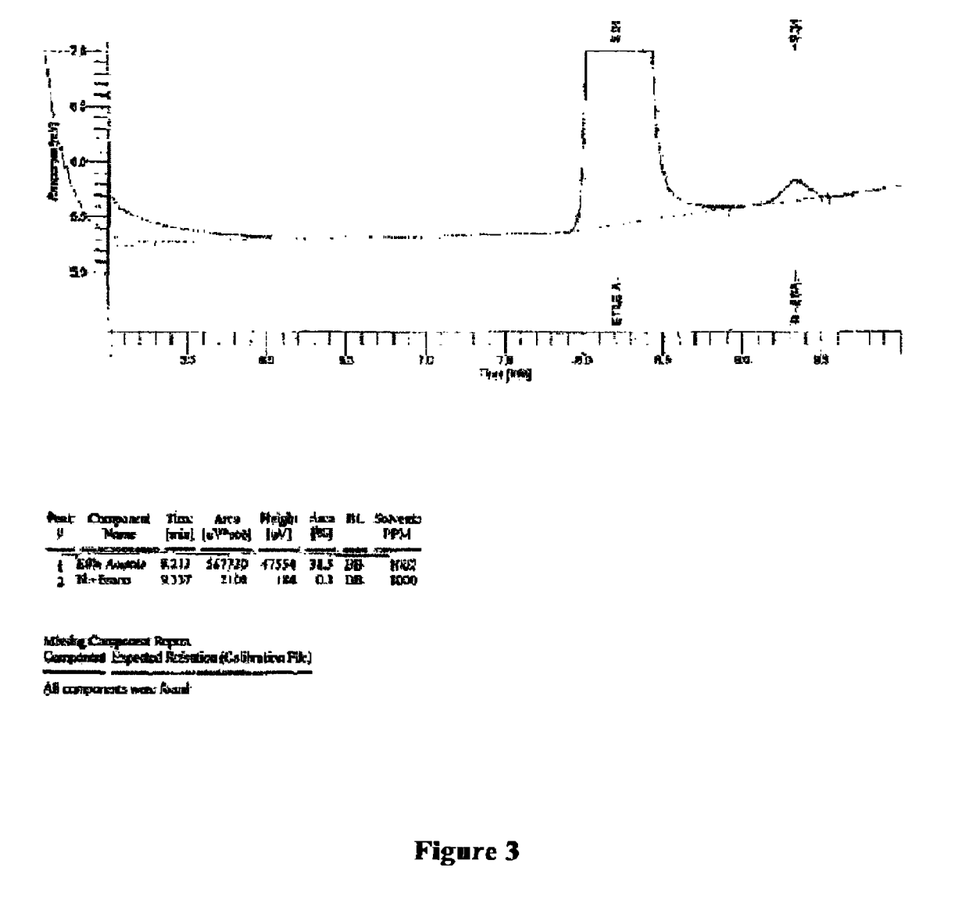
FIG. 3 is a calibration of chromatogram obtained using a standard consisting of ethyl acetate and n-hexane corresponding to 1000 ppm each, equivalent to 100 mg of test product.

The calibration chromatogram (FIG. 3) was obtained using a standard consisting of ethyl acetate and n-hexane corresponding to 1000 ppm each, equivalent to 100 mg of test product.

Figure 4:
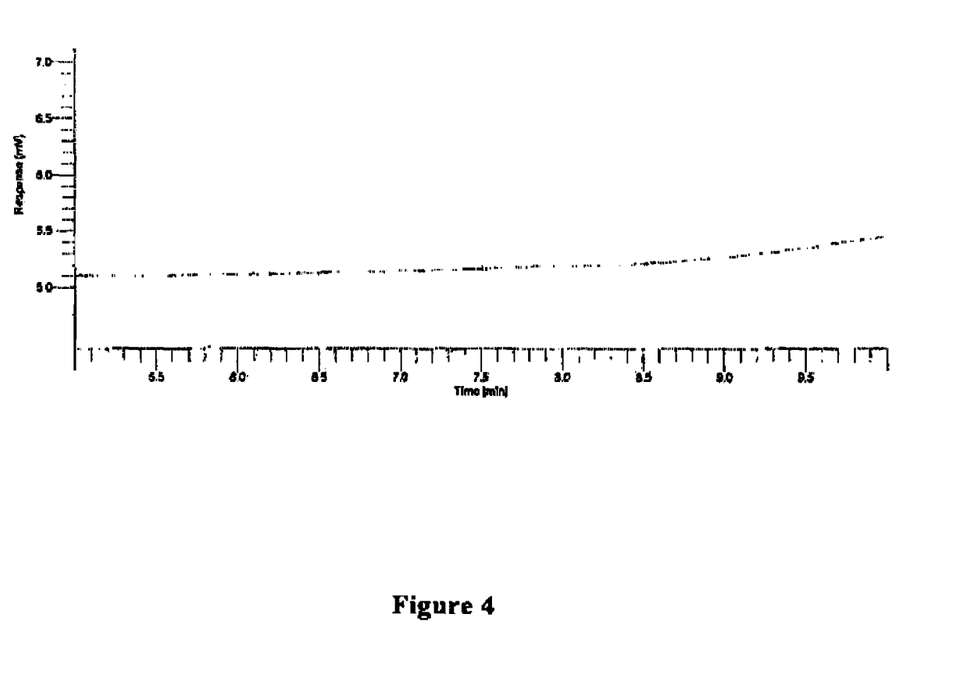
FIG. 4 is a graph of the chromatographic analysis of phosphatidylserine (PS) purified according to method 1.

FIG. 4 shows the total absence of n-hexane in the PS purified according to Method 1.

EXAMPLE 6

Separation and Purification of PS According to Method 2

The reaction medium in which the PS was prepared is supplemented with 1.5 volumes (in terms of the starting reaction volume) of a solution of 5% NaCl and the whole is stirred at 45° C. for at least 30 minutes, followed by a period of separation of the PS lasting at least 1 hour.

Two phases are formed: they are separated and the subnatant is discarded, while the supernatant is supplemented with 2.5 volumes of a solution of EDTA 22 gg/liter, prepared in water. Once a temperature of 28° C. has been reached, ultrafiltration is performed. Preferably, filters should be used that have pores of a size that will trap molecules with a molecular weight of 100,000/300,000 Daltons should be used.

The final product can then be freeze-dried.

Final product: distribution of the lipid fractions isolated according to method 2, with PS prepared, for example, according to Example 1 with CaO 0.54M.
PA 6.0%
PS 94.0%

The concentration of serine was measured at the end of the PS purification process previously described and proved to be lower than/equal to 0.2%, while further determination of the residue activity of the PLD enzyme showed it to be below the limit for determination by this method.

The invention claimed is:

1. A process for the preparation of phosphatidylserine of formula wherein $R^1$ and $R^2$ independently represent a saturated, mono-unsaturated or polyunsaturated acyl $C_{10}$-$C_{30}$, X=OH or OM where M=alkaline or alkaline earth metal, ammonium, alkylammonium (including the inner salt) including the transphosphatidylation reaction between a compound of the general formula wherein $R^1$ and $R^2$ and X have the above specified meanings, $R^3 = CH_2—CH_2—NH_2$ or $CH_2—CH_2—N^+(CH_3)_3$ and Serine in D, L or racemic form catalysed by the phospholipase D enzyme (PLD),
characterised in that said reaction is carried out in a hydroalcoholic medium containing an aliphatic alcohol and in the presence of bivalent metal oxide.

2. The process according to claim 1 wherein the aliphatic alcohols are selected from methanol, ethanol, n-propanol and isopropanol.

3. The process according to claim 2 wherein the aliphatic alcohol is isopropanol in a concentration between 0.1 and 50% expressed as a % by volume on the volume of the starting buffer.

4. The process according to claim 3 wherein isopropanol concentration is 10%.

5. The process according to claim 1 wherein the compound is phosphatidylcholine and the concentration of serine ranges between 1 and 5 gg/gg of phosphatidylcho line.

6. The process according to claim 5 wherein the compound is phosphatidylcholine and the concentration of serine ranges between 2 and 3 gg/gg of phosphatidylcho line.

7. The process according to claim 1 wherein the compound is phosphatidylcholine and the phosphatidylcholine is of animal and/or vegetal origin, natural or synthetic, present in purified form or as raw material, at an starting concentration of between 10 and 500 mg/ml.

8. The process according to claim 1 wherein the transphosphatidylation reaction occurs at a temperature of between 20° C. and 60° C.

9. The process according to claim 8 wherein the transphosphatidylation reaction occurs at a temperature of 45° C.

10. The process according to claim 1 wherein the enzyme PLD is of fermentative origin derived from the micro-organism *Streptoverticillium hachijoense*, used in purified, partially purified or non-purified form.

11. The process according to claim 10 wherein the compound is phosphatidylcholine and the concentration of PLD that is used varies between 1 and 100 units/g of phosphatidylcholine.

12. The process according to claim 11 wherein the compound is phosphatidylcholine and the concentration of PLD that is used varies between 1 and 10 units/g of phosphatidylcholine.

13. The process for the purification of phosphatidylserine (PS) produced according claim 1 and involving the following steps:
I) adding a saline solution of sodium chloride to the reaction medium containing the PS that has been produced, with the subsequent mixing and separation of the PS;
II) collection and elimination of the subnatant;
III) steps I and II can be repeated modifying the starting concentration of sodium chloride solution and eliminating the supernatant;
IV) adding a solution of EDTA to chelate the ions present in the solution, and subsequent mixing;
V) adding a ethanol solution consisting of ethanol at a percentage of 50 to 100% or a mixture of acetone/water consisting of acetone at a percentage of 50 to 95% with subsequent mixing and sedimentation of the PS;
VI) step V can be repeated modifying the percentage of ethanol;
VII) adding a ethanol solution consisting of ethanol at a percentage of 90 to 100%;
VIII) collection and elimination of the supernatant;
IX) drying to the final product obtained.

14. The process for the purification of phosphatidylserine (PS) produced according to claim 1 comprising the following steps:
I) adding a saline solution of sodium chloride to the PS that has been previously filtered, with the subsequent mixing and separation of the PS;
II) collection and elimination of the supernatant;
III) steps I and II can be repeated modifying the starting concentration of sodium chloride solution and eliminating the supernatant;
IV) adding a solution of EDTA to chelate the ions present in the solution, and subsequent mixing;
V) adding a ethanol solution consisting of ethanol at a percentage of 50 to 100% or a mixture of acetone/water consisting of acetone at a percentage of 50 to 95% with subsequent mixing and sedimentation of the PS;
VI) step V can be repeated modifying the percentage of ethanol;
VII) adding a ethanol solution consisting of ethanol at a percentage of 90 to 100%;
VIII) collection and elimination of the supernatant;
IX) drying to the final product obtained.

15. The process for the purification of phosphatidylserine (PS) produced according to claim 1 comprising the following steps:
I) adding a saline solution of sodium chloride to the reaction medium containing the PS that has been produced, with subsequent mixing and separation of the PS;
II) collection and elimination of the subnatant;
III) adding a saline solution of sodium chloride and performing ultrafiltration through a porous membrane;
IV) drying the final product.

16. The process according to claim 10 wherein the enzyme PLD derived from the micro-organism *Streptoverticillium hachijoense* is purified involving the following steps:
I) elimination of the producing agent by microfiltration with a pore size of 0.2 μm;
II) ultrafiltration through filters with a molecular cut-off of 10,000 D;
III) ultrafiltration through filters with membranes with a molecular cut-off of 300,000 D;
IV) ultrafiltration through membranes with a molecular cut-off of 10,000 D to re-concentrate the enzyme and dialyse it against acidic buffer.

17. The process according to claim 7 wherein the starting concentration is between 200 and 300 mg/ml.

18. The process according to claim 8 wherein the transphosphatidylation reaction occurs at a temperature of 55° C.

19. A process for the preparation of phosphatidylserine of formula wherein $R^1$ and $R^2$ independently represent a saturated, mono-unsaturated or polyunsaturated acyl $C_{10}$-$C_{30}$, X=OH or OM where M=alkaline or alkaline earth metal, ammonium, alkylammonium (including the inner salt) including the transphosphatidylation reaction between a compound of the general formula wherein $R^1$ and $R^2$ and X have the above specified meanings, $R^3=CH_2-CH_2-NH_2$ or $CH_2-CH_2-N^+(CH_3)_3$ and Serine in D, L or racemic form catalysed by the phospholipase D enzyme (PLD), characterised in that said reaction occurs in a medium containing an aprotic polar solvent and in the presence of a bivalent metal oxide.

20. The process according to claim 19 wherein the aprotic polar solvents are selected from dimethylsulphoxide, acetonitrile, dimethylformamide and N-methyl-pyrrolidone.

21. The process according to claim 20 wherein the aprotic polar solvent is dimethylsulphoxide in a concentration between 0.1 and 50% expressed as a % by volume on the volume of the starting buffer.

22. The process according to claim 21 wherein dimethylsulphoxide concentration is 1.25%.

23. The process according to claim 20 wherein the bivalent metal oxide is calcium or magnesium or zinc oxide in a concentration between 0.1 and 1M.

24. The process according to claim 23 wherein the concentration of the selected oxides is 0.33 or 0.54 M.

25. A process for the preparation of phosphatidylserine of formula wherein $R^1$ and $R^2$ independently represent a saturated, mono-unsaturated or polyunsaturated acyl $C_{10}$-$C_{30}$, X=OH or OM where M=alkaline or alkaline earth metal, ammonium, alkylammonium (including the inner salt) including the transphosphatidylation reaction between a compound of the general formula wherein $R^1$ and $R^2$ and X have the above specified meanings, $R^3=CH_2-CH_2-NH_2$ or $CH_2-CH_2-N^{30}(CH_3)_3$ and Serine in D, L or racemic form catalysed by the phospholipase D enzyme (PLD), characterised in that said reaction is carried out in a medium consisting of a two-phase system formed by water/organic solvent and in the presence of bivalent metal oxide.

26. The process according to claim 25 wherein the organic solvents are selected from n-hexane, toluene, benzene and n-butanol.

27. The process according to claim 26 wherein the organic solvent is n-hexane in a concentration between 0.1 and 40% expressed as % by volume on the volume of the starting buffer.

28. The process according to claim 27 wherein n-hexane concentration is 1.25% or 2.5%.

29. The process according to claim 19 wherein the bivalent metal oxide is calcium or magnesium or zinc oxide in a concentration between 0.1 and 1M.

30. The process according to claim 19 wherein the compound is phosphatidylcholine and the concentration of serine ranges between 1 and 5 gg/gg of phosphatidylcholine.

31. The process according to claim 19 wherein the compound is phosphatidylcholine and the phosphatidylcholine is of animal and/or vegetal origin, natural or synthetic, present in purified form or as raw material, at an starting concentration of between 10 and 500 mg/ml.

32. The process according to claim 2 wherein the transphosphatidylation reaction occurs at a temperature of between 20° C. and 60° C.

33. The process according to claim 2 wherein the enzyme PLD is of fermentative origin derived from the micro-organism *Streptoverticillium hachijoense*, used in purified, partially purified or non-purified form.

34. The process for the purification of phosphatidylserine (PS) produced according claim 2 and involving the following steps:
   I) adding a saline solution of sodium chloride to the reaction medium containing the PS that has been produced, with the subsequent mixing and separation of the PS;
   II) collection and elimination of the subnatant;
   III) steps I and II can be repeated modifying the starting concentration of sodium chloride solution and eliminating the supernatant;
   IV) adding a solution of EDTA to chelate the ions present in the solution, and subsequent mixing;
   V) adding a ethanol solution consisting of ethanol at a percentage of 50 to 100% or a mixture of acetone/water consisting of acetone at a percentage of 50 to 95% with subsequent mixing and sedimentation of the PS;
   VI) step V can be repeated modifying the percentage of ethanol;
   VII) adding a ethanol solution consisting of ethanol at a percentage of 90 to 100%;
   VIII) collection and elimination of the supernatant;
   IX) drying to the final product obtained.

35. The process for the purification of phosphatidylserine (PS) produced according to claim 19 comprising the following steps:
- I) adding a saline solution of sodium chloride to the PS that has been previously filtered, with the subsequent mixing and separation of the PS;
- II) collection and elimination of the supernatant;
- III) steps I and II can be repeated modifying the starting concentration of sodium chloride solution and eliminating the supernatant;
- IV) adding a solution of EDTA to chelate the ions present in the solution, and subsequent mixing;
- V) adding a ethanol solution consisting of ethanol at a percentage of 50 to 100% or a mixture of acetone/water consisting of acetone at a percentage of 50 to 95% with subsequent mixing and sedimentation of the PS;
- VI) step V can be repeated modifying the percentage of ethanol;
- VII) adding a ethanol solution consisting of ethanol at a percentage of 90 to 100%;
- VIII) collection and elimination of the supernatant;
- IX) drying to the final product obtained.

36. The process for the purification of phosphatidylserine (PS) produced according to claim 19 comprising the following steps:
- I) adding a saline solution of sodium chloride to the reaction medium containing the PS that has been produced, with subsequent mixing and separation of the PS;
- II) collection and elimination of the subnatant;
- III) adding a saline solution of sodium chloride and performing ultrafiltration through a porous membrane;
- IV) drying the final product.

37. The process according to claim 25 wherein the bivalent metal oxide is calcium or magnesium or zinc oxide in a concentration between 0.1 and 1M.

38. The process according to claim 25 wherein the compound is phosphatidylcholine and the concentration of serine ranges between 1 and 5 gg/gg of phosphatidylcholine.

39. The process according to claim 25 wherein the compound is phosphatidylcholine and the phosphatidylcholine is of animal and/or vegetal origin, natural or synthetic, present in purified form or as raw material, at an starting concentration of between 10 and 500 mg/ml.

40. The process according to claim 25 wherein the transphosphatidylation reaction occurs at a temperature of between 20° C. and 60° C.

41. The process according to claim 25 wherein the enzyme PLD is of fermentative origin derived from the micro-organism *Streptoverticillium hachijoense*, used in purified, partially purified or non-purified form.

42. The process for the purification of phosphatidylserine (PS) produced according claim 25 and involving the following steps:
- I) adding a saline solution of sodium chloride to the reaction medium containing the PS that has been produced, with the subsequent mixing and separation of the PS;
- II) collection and elimination of the subnatant;
- III) steps I and II can be repeated modifying the starting concentration of sodium chloride solution and eliminating the supernatant;
- IV) adding a solution of EDTA to chelate the ions present in the solution, and subsequent mixing;
- V) adding a ethanol solution consisting of ethanol at a percentage of 50 to 100% or a mixture of acetone/water consisting of acetone at a percentage of 50 to 95% with subsequent mixing and sedimentation of the PS;
- VI) step V can be repeated modifying the percentage of ethanol;
- VII) adding a ethanol solution consisting of ethanol at a percentage of 90 to 100%;
- VIII) collection and elimination of the supernatant;
- IX) drying to the final product obtained.

43. The process for the purification of phosphatidylserine (PS) produced according to claim 25 comprising the following steps:
- I) adding a saline solution of sodium chloride to the PS that has been previously filtered, with the subsequent mixing and separation of the PS;
- II) collection and elimination of the supernatant;
- III) steps I and II can be repeated modifying the starting concentration of sodium chloride solution and eliminating the supernatant;
- IV) adding a solution of EDTA to chelate the ions present in the solution, and subsequent mixing;
- V) adding a ethanol solution consisting of ethanol at a percentage of 50 to 100% or a mixture of acetone/water consisting of acetone at a percentage of 50 to 95% with subsequent mixing and sedimentation of the PS;
- VI) step V can be repeated modifying the percentage of ethanol;
- VII) adding a ethanol solution consisting of ethanol at a percentage of 90 to 100%;
- VIII) collection and elimination of the supernatant;
- IX) drying to the final product obtained.

44. The process for the purification of phosphatidylserine (PS) produced according to claim 25 comprising the following steps:
- I) adding a saline solution of sodium chloride to the reaction medium containing the PS that has been produced, with subsequent mixing and separation of the PS;
- II) collection and elimination of the subnatant;
- III) adding a saline solution of sodium chloride and performing ultrafiltration through a porous membrane;
- IV) drying the final product.

* * * * *

UNITED STATES PATENT AND TRADEMARK OFFICE
CERTIFICATE OF CORRECTION

| | | |
|---|---|---|
| PATENT NO. | : 7,759,095 B2 | Page 1 of 1 |
| APPLICATION NO. | : 11/922680 | |
| DATED | : July 20, 2010 | |
| INVENTOR(S) | : Anna Maria Zanellato et al. | |

It is certified that error appears in the above-identified patent and that said Letters Patent is hereby corrected as shown below:

Column 16, line 11 reading:

"ings, $R^3=CH_2-CH_2-NH_2$ or $CH_2-CH_2-N^{30}$" should read --ings, $R^3=CH_2-CH_2-NH_2$ or $CH_2-CH_2-N^+$--

Column 16, line 38 reading:

"32. The process according to claim 2 wherein the transpho-" should read --32. The process according to claim 19 wherein the transpho- --

Column 16, line 41 reading:

"33. The process according to claim 2 wherein the enzyme" should read --33. The process according to claim 19 wherein the enzyme--

Column 16, line 46 reading:

"(PS) produced according claim 2 and involving the following" should read --(PS) produced according claim 19 and involving the following--

Signed and Sealed this
Twenty-second Day of May, 2012

David J. Kappos
*Director of the United States Patent and Trademark Office*